United States Patent
Bafaqeer et al.

(10) Patent No.: US 12,221,408 B1
(45) Date of Patent: Feb. 11, 2025

(54) PHOTOCATALYTIC REDUCTION OF CARBON DIOXIDE USING $Fe_2TiO_5$ NANOSHEETS

(71) Applicant: KING FAHD UNIVERSITY OF PETROLEUM AND MINERALS, Dhahran (SA)

(72) Inventors: Abdullah Salem Mohammed Bafaqeer, Dhahran (SA); Aniz Chennampilly Ummer, Dhahran (SA)

(73) Assignee: KING FAHD UNIVERSITY OF PETROLEUM AND MINERALS, Dhahran (SA)

( * ) Notice: Subject to any disclaimer, the term of this patent is extended or adjusted under 35 U.S.C. 154(b) by 0 days.

(21) Appl. No.: 18/786,055

(22) Filed: Jul. 26, 2024

(51) Int. Cl.
C07C 41/01 (2006.01)
C07C 29/15 (2006.01)

(52) U.S. Cl.
CPC ............. C07C 41/01 (2013.01); C07C 29/15 (2013.01)

(58) Field of Classification Search
CPC ................................ C07C 41/01; C07C 29/15
See application file for complete search history.

(56) References Cited

U.S. PATENT DOCUMENTS

| | | | |
|---|---|---|---|
| 9,868,636 B1 | 1/2018 | Coker et al. | |
| 2014/0179810 A1* | 6/2014 | Yoon | B01J 19/127 518/711 |
| 2014/0235736 A1 | 8/2014 | Yoon | |
| 2023/0381767 A1 | 11/2023 | Pagis et al. | |

OTHER PUBLICATIONS

Min et al., Synthesis of pseudobrookite-type Fe2TiO5 nanoparticles and their Li-ion electroactivity, Ceramics International vol. 38, Issue 7, Sep. 2012, pp. 6009-6013.*

Ankit Mishra, et al., "Waste ilmenite sludge-derived low-cost mesoporous Fe-doped TiO2: A versatile photocatalyst for enhanced visible light photocatalysis without a cocatalyst", Journal of Environmental Chemical Engineering, vol. 11, Issue 5, Oct. 2023, 6 pages total.

Quang Duc Truong, et al., "Photocatalytic reduction of CO2 on FeTiO3/TiO2 photocatalyst", Catalysis Communications, vol. 19, Mar. 2012, 5 pages total.

* cited by examiner

*Primary Examiner* — Jafar F Parsa
(74) *Attorney, Agent, or Firm* — Oblon, McClelland, Maier & Neustadt, L.L.P.

(57) ABSTRACT

A method of reducing carbon dioxide ($CO_2$) including contacting a catalyst and the $CO_2$ and irradiating the catalyst and the $CO_2$ with visible light. Upon irradiating the $CO_2$ is reduced to a conversion product. The catalyst includes $Fe_2TiO_5$ in the form of nanosheets. The nanosheets have an average width of 200 nanometers (nm) to 800 nm and form a hierarchical structure.

18 Claims, 13 Drawing Sheets

PHOTOCATALYTIC REDUCTION OF CARBON DIOXIDE USING $Fe_2TiO_5$ NANOSHEETS

STATEMENT OF ACKNOWLEDGEMENT

Support provided by the King Fahd University of Petroleum and Minerals (KFUPM) is gratefully acknowledged.

BACKGROUND

Technical Field

The present disclosure is directed towards reducing carbon dioxide ($CO_2$), and more particularly, towards a method of reducing $CO_2$ using $Fe_2TiO_5$ nanosheets.

Description of Related Art

The "background" description provided herein is to present the context of the disclosure generally. Work of the presently named inventors, to the extent it is described in this background section, as well as aspects of the description that may not otherwise qualify as prior art at the time of filing, are neither expressly nor impliedly admitted as prior art against the present invention.

Burning of fossil fuels produces greenhouse gases such as $CO_2$, NO, and $CH_4$, which negatively impacts the environment. Therefore, $CO_2$ reduction into useful carbon sources such as, $CH_3OH$, dimethyl ether (DME) and $CH_4$, is a positive approach for a robust environmental value-added chemical production and energy storage infrastructure. The electrochemical reduction of $CO_2$ requires improvements in regard to control of product selectivity, the enhancement of product conversion rate, and the minimal needed overpotential. Typically, this process includes numerous proton and electron transfers, thus producing various products, each with several likely reaction intermediates. This complexity poses significant drawbacks in the characterization of molecular-level reaction mechanisms, which are demanding in the design of selective, effective electrodes and stable electrocatalysts.

Materials employed in electrochemical reduction should be available in large quantities with significant efficiency while preserving low costs to ensure their economic viability. Furthermore, favorable properties include high $CO_2$ adsorption capacity, efficient charge transfer kinetics, and the ability to suppress competing reactions. The catalysts should exhibit long-term stability, allowing continuous $CO_2$ reduction under various operating conditions. To date, different electrode materials and designs have been investigated for the electrochemical reduction of $CO_2$, with materials such as metal nanoparticles, metal-organic frameworks, and single-atom catalysts.

Specifically, the use of solar energy for photocatalytic $CO_2$ conversion into high-value fuels is highly desirable. Photocatalysts such as $TiO_2$, $Fe_2O_3$, ZnO, $Ta_2O_5$ and $WO_3$ have been developed and $TiO_2$ has garnered attention as a semiconductor because of its strong oxidation and reduction abilities. Additionally, $TiO_2$ is eco-friendly, affordable, and may be produced in diverse nanostructures using economical techniques. However, a high rate of charge recombination leads to inadequate photocatalytic capabilities. Hence, enhancing the light absorption capacity of $TiO_2$ to encompass the visible range of the solar spectrum can improve photocatalytic capabilities. To address this issue, several strategies have been explored, including the application of noble metals, surface sensitization to light, and the creation of carbon-based composites.

An approach to boost $TiO_2$ activity under visible light involves incorporating semiconductors with a low band gap energy. This combination extends the optical absorption range into the visible portion of the solar spectrum. Iron (III) oxide ($Fe_2O_3$), with its narrow band gap of around 1.97 electron Volts (eV) emerges as an option for this purpose. The development of a combined $Fe_2TiO_5$ nanostructures may improve both photoactivity and selectivity when compared to only a mixture of the $Fe_2O_3/TiO_2$ materials.

Accordingly, an object of the present disclosure is to develop a $Fe_2TiO_5$ nanomaterial for $CO_2$ reduction, particularly under solar energy conditions.

SUMMARY

In an exemplary embodiment, a method of reducing carbon dioxide is described. The method includes contacting a catalyst and the carbon dioxide ($CO_2$) and irradiating the catalyst and the $CO_2$ with visible light. Further, on irradiating, the $CO_2$ is reduced to a conversion product. The catalyst includes $Fe_2TiO_5$ and particles of the $Fe_2TiO_5$ are in a form of nanosheets. The nanosheets have an average width of 200 nanometers (nm) to 800 nm, and the nanosheets form a hierarchical structure.

In some embodiments, the nanosheets are crystalline.

In some embodiments, the nanosheets have an interplanar distance of 0.3-0.4 nm.

In some embodiments, the nanosheets have an average length of 1 micrometers (μm) to 3 μm.

In some embodiments, the catalyst includes 45 weight percentage (wt. %) to 55 wt. % Fe, 25-35 wt. % 0, and 15-25 wt. % Ti, based on a total weight of the catalyst.

In some embodiments, the catalyst absorbs light from 200-550 nm.

In some embodiments, the catalyst has a peak light absorbance from 375-425 nm.

In some embodiments, the catalyst has a band gap of 1.9 electron Volts (eV) to 2.2 eV.

In some embodiments, the catalyst does not include $Fe_2O_3$ or $TiO_2$.

In some embodiments, the carbon dioxide is in a gaseous state.

In some embodiments, the carbon dioxide is in an aqueous solution.

In some embodiments, the conversion product is at least one selected from the group consisting of methanol and dimethyl ether.

In some embodiments, the iriadiating is for 1 min to 10 hours.

In some embodiments, the visible light has a wavelength of 400-700 nm, and a power of 10-100 W.

In some embodiments, the conversion product is methanol, and a yield of the methanol is 120 micromoles per gram (μmol/g) to 160 μmol/g of the catalyst after irradiating for 4 hours.

In some embodiments, the conversion product is dimethyl ether, and a yield of the dimethyl ether of 40-60 μmol/g of the catalyst after irradiating for 4 hours.

In some embodiments, the catalyst has a higher conversion to the conversion product than $TiO_2$ under the same conditions.

In another exemplary embodiment, a method for making the $Fe_2TiO_5$ catalyst is described.

The method includes mixing an iron salt in a solvent to form a first mixture, adding titanium isopropoxide to the first mixture to form a second mixture, and heating the second mixture in an autoclave at a temperature of 150 degrees Celsius (° C.) 200° C. for 1-24 hours to form a suspension.

The method further includes separating a precipitate from the suspension and calcining the precipitate at a temperature of 400-800° C. for 1-24 hours to form the catalyst.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

Figure 1A:
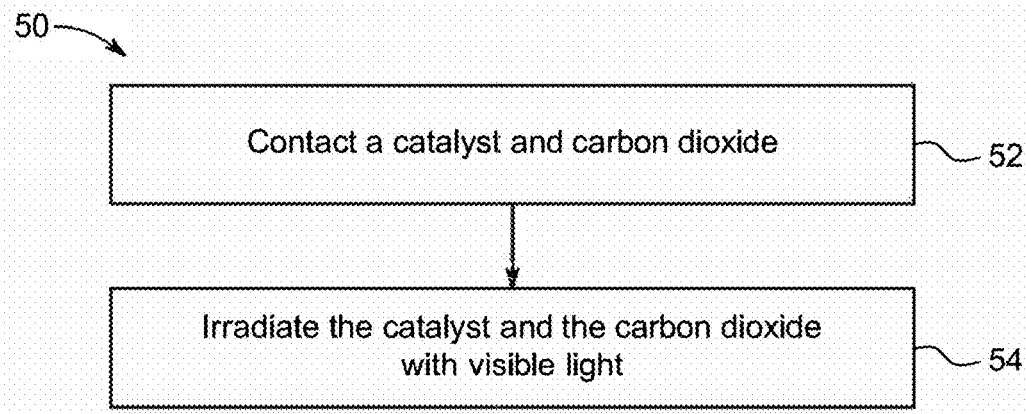
FIG. 1A is a flowchart illustrating a method for reducing carbon dioxide, according to certain embodiments.

In the drawings, reference numerals designate identical or corresponding parts throughout the several views. Further, as used herein, the words "a," "an," and the like generally carry a meaning of "one or more," unless stated otherwise.

Furthermore, the terms "approximately," "approximate," "about," and similar terms generally refer to ranges that include the identified value within a margin of 20%, 10%, or preferably 5%, and any values therebetween.

Where a numerical limit or range is stated herein, the endpoints are included. Also, all values and subranges within a numerical limit or range are specifically included as if explicitly written out.

Aspects of the present disclosure are directed toward a method of reducing carbon dioxide ($CO_2$) using a $Fe_2TiO_5$ nanomaterial. The nanomaterial of the present disclosure, synthesized via a single-step hydrothermal method, functions as an efficient photocatalyst capable of responding to visible light for $CO_2$ conversion.

FIG. 1A illustrates a schematic flow chart of a method 50 of reducing carbon dioxide. The order in which the method 50 is described is not intended to be construed as a limitation, and any number of the described method steps can be combined in any order to implement the method 50. Additionally, individual steps may be removed or skipped from the method 50 without departing from the spirit and scope of the present disclosure.

At step 52, the method 50 includes contacting a catalyst and carbon dioxide ($CO_2$). The catalyst includes $Fe_2TiO_5$. Particles of the $Fe_2TiO_5$ are in the form of nanosheets, although in some embodiments, the particles may exist in various morphological shapes, such as nanowires, nanocrystals, nanorectangles, nanotriangles, nanopentagons, nanohexagons, nanoprisms, nanodisks, nanocubes, nanoribbons, nanoblocks, nanobeads, nanotoroids, nanodiscs, nanobarrels, nanogranules, nanowhiskers, nanoflakes, nanofoils, nanopowders, nanoboxes, nanostars, tetrapods, nanobelts, nano-urchins, nanoflowers, etc. and mixtures thereof.

In some embodiments, the nanosheets have an average width of 200-800 nanometers (nm), preferably 250-750 nm, 300-700 nm, 350-650 nm, 400-600 nm, or 450-550 nm. In some embodiments, the nanosheets have an average length of 1-3 micrometers (μm), preferably 1.2-2.8 μm, 1.4-2.6 μm, 1.6-2.4 μm, 1.8-2.2 μm, or about 2 μm. In some embodiments, the nanosheets form a hierarchical structure, where the nanosheets are stacked on top of one another forming a column of the nanosheets. The nanosheets form a hierarchical structure of two or more of the nanosheets stacked on top of one another, preferably 2 to 10,000 nanosheets, 10-1,000 or 100-500 nanosheets. In some embodiments, the interplanar distance between the nanosheets is between 0.3-0.4 nm, more preferably 0.32-0.38 nm, and yet more preferably 0.35 nm. In some embodiments, the columns of nanosheets are randomly oriented. In some embodiments, the nanosheet columns are organized and are evenly spaced parallel to one another.

In some embodiments, the nanosheets are crystalline. In some embodiments, the nanosheets consist of a $Fe_2TiO_5$ crystalline phase. In some embodiments, the catalyst does not include $Fe_2O_3$ or $TiO_2$ crystalline phases.

The $Fe_2TiO_5$ catalyst includes 45-55 wt. %, more preferably 51 to 53 wt. %, and yet more preferably 52.9 wt. % Fe, 25-35 wt. %, more preferably 28 to 32 wt. %, and yet more preferably 29.7 wt. % 0, and 15-25 wt. %, more preferably 16 to 18 wt. %, and yet more preferably 17.4 wt. % Ti, based on the total weight of the catalyst.

The catalyst is contacted with $CO_2$, preferably in a reactor. In some embodiments, the carbon dioxide is in a gaseous state. The reactor may optionally include other gases as well, such as CO or hydrogen. In some embodiments, the reactor is purged with an inert gas or nitrogen to remove other gases before contacting the catalyst with the $CO_2$. After purging, the catalyst is placed in the reactor, preferably as powdered particles, to ensure proper distribution. The $CO_2$ is flowed into the reactor at a flow rate in the range of 5-20 mL/min, preferably 6-19 mL/min, preferably 7-18 mL/min, preferably 8-15 mL/min, preferably 10-12 mL/min, preferably 10 mL/min.

In some embodiments, the carbon dioxide is in an aqueous solution. The aqueous solution may be tap water, distilled water, bi-distilled water, deionized water, deionized distilled water, reverse osmosis water, and/or some other water. In some embodiments, the aqueous solution contains 0.1-100 ppm of the carbon dioxide, preferably 1-90 ppm, 10-80 ppm, 20-70 ppm, 30-60 ppm, and 40-50 ppm. The $CO_2$ in the aqueous solution is flowed into the reactor at a flow rate in the range of 1-100 mL/min, preferably 10-90 mL/min, preferably 20-80 mL/min, preferably 30-70 mL/min, preferably 40-60 mL/min, preferably 50 mL/min.

The reactor is at least one selected from the group consisting of a fixed-bed reactor, a trickle-bed reactor, a moving bed reactor, a rotating bed reactor, a fluidized bed reactor, and a slurry reactor. In the present disclosure, the reactor is a fixed-bed reactor in the form of a cylindrical reactor, which includes a top portion, a cylindrical body portion, a bottom portion, and a housing. As used herein, the term 'fixed-bed reactor' refers to the cylindrical tube filled with catalyst pellets with reactants flowing through the bed and being converted into products.

At step 54, method 50 includes irradiating the catalyst and the carbon dioxide with light. The steps 52 and 54 may occur simultaneously. In a preferred embodiment, the light is visible light. As used herein, "visible light" refers to light having a wavelength λ greater than 400 nm, preferably 400-700 nm, preferably 500-600 nm, preferably 510-590 nm, preferably 520-580 nm, preferably 530-580 nm, preferably 550-580 nm, preferably 570-590 nm, preferably 580-590 nm, preferably 587 nm. The irradiation process is carried out under visible light at a power of 10-100 watts (W), preferably 20-90 W, preferably 30-80 W, preferably 40-60 W, and yet more preferably 50 W for 1 minute to 10 hours, preferably 1 to 9 hours, 2 to 8 hours, 3 to 7 hours, 4 to 6 hours, or 5 hours.

The catalyst has a band gap of 1.9-2.2 electron volts (eV), preferably 1.95-2.15 eV, 2.0-2.1 eV, or about 2.05 eV. The catalyst absorbs light from 200 to 550 nm, preferably 250-500 nm, 300-450 nm, or 350-400 nm, with a peak light absorbance in the range of 375 to 425 nm or about 400 nm. The addition of the Fe into the crystal structure improves the absorption of visible light in comparison to $TiO_2$ alone which does not absorb light after about 400 nm.

Upon the absorption of light by the $Fe_2TiO_5$ catalyst, photoexcitation occurs, resulting in photoreduction of $CO_2$ to form conversion products. In some embodiments, the conversion product is selected from the group consisting of methane, hydrogen, carbon monoxide, methanol and dimethyl ether. The hydrogen source for the photoreduction process may be water, hydrogen, or other appropriate sources that produce atomic hydrogen known in the art.

The yield of methanol is 120-160 μmol per gram of the catalyst, more preferably 140-155 μmol per gram of the catalyst, and yet more preferably 149.5 μmol per gram of the catalyst after irradiation for 4 hours, and the yield of the dimethyl ether is about 40-60 μmol per gram of the catalyst after irradiation for 4 hours. In some embodiments, the conversion reaction continues for at least 4 hours, preferably 4-24 hours, 5-20 hours, or 10-15 hours. In other words, the catalyst is stable and does not degrade over such time period.

In some embodiments, if the catalyst and carbon dioxide are contacted and not irradiated, the conversion products are not generated. In other words, the catalyst acts as a photocatalyst and is not activated without the absorption of light.

In some embodiments, the $Fe_2TiO_5$ catalyst has a higher conversion to the conversion product than $TiO_2$ under the same conditions. While not wishing to be bound to a single theory, this improvement is ascribed to the effective absorption of visible light by the $Fe_2TiO_5$, proficient charge transfer characteristics, and heightened electron mobility achieved through the coupling of iron with titanium and the formation of a hierarchical structure.

Figure 1B:
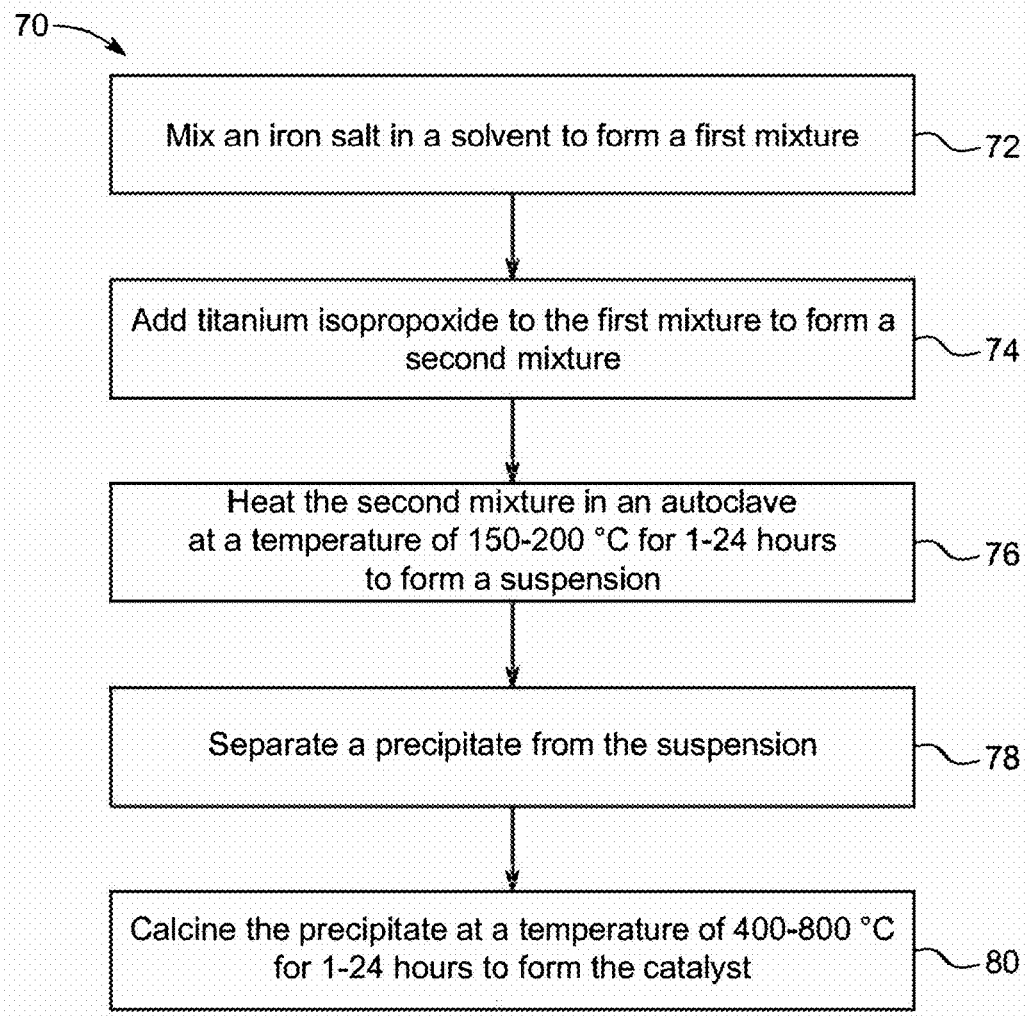
FIG. 1B is a flowchart illustrating a method of making $Fe_2TiO_5$, according to certain embodiments.

FIG. 1B illustrates a schematic flow chart of a method 70 of making the $Fe_2TiO_5$. The order in which the method 70 is described is not intended to be construed as a limitation, and any number of the described method steps can be combined in any order to implement the method 70. Additionally, individual steps may be removed or skipped from the method 70 without departing from the spirit and scope of the present disclosure.

At step 72, the method 70 includes mixing an iron salt in a solvent to form a first mixture. Suitable examples of iron salts include iron (II) acetate, iron (II) bromide, iron (II) carbonate, iron (II) chloride, iron (II) chromite, iron (II) citrate, iron (II) cyanide, iron (II) fluoride, iron (II) fumarate, iron (II) gluconate, iron (II) hydride, iron (II) hydroxide, iron (II) iodide, iron (II) lactate, iron (II) molybdate, iron (II) nitrate, iron (II) oxalate, iron (III) chloride, iron (III) thiocyanate, ferric sulfate, ferrous fumarate, ferrous gluconate, ferrous succinate, iron (III) hydroxide, iron (III) nitrate. In some embodiments, the iron salt is iron (III) nitrate. In some embodiments, the solvent is an organic solvent. In some embodiments, the solvent may include, but is not limited to, tetrahydrofuran, ethyl acetate, dimethylformamide, acetonitrile, acetone, dimethyl sulfoxide, nitromethane, propylene carbonate, ethanol, formic acid, n-butanol, methanol, or any combination thereof. In some embodiments, the solvent may include benzene, cyclohexane, ethanol, methanol, acetone, ethyl acetate, dichloromethane, toluene, and diethyl ether. In a preferred embodiment, the solvent is isopropanol. The iron salt may be mixed with the solvent via stirring/swirling/sonication/a combination of these methods to form the first mixture.

At step 74, the method 70 includes adding titanium isopropoxide to the first mixture to form a second mixture. Titanium isopropoxide can be added dropwise to the first mixture. In some embodiments, the titanium isopropoxide can be added to the first mixture by any method used or known in the art.

At step 76, the method 70 includes heating the second mixture in an autoclave, preferably a Teflon-lined stainless-steel autoclave, at a temperature of 150-200° C., more preferably 155 to 165° C., and more preferably 160° C. for 1-24 hours, more preferably 10 to 14 hours, and more preferably 12 hours to form a suspension. In some embodiments, the heating can be performed by using heating appliances such as ovens, microwaves, autoclaves, hot plates, heating mantles and tapes, oil baths, salt baths, sand baths, air baths, hot-tube furnaces, and hot-air guns.

At step 78, method 70 includes separating a precipitate from the suspension. The separation may be performed by methods including filtration, decantation, evaporation, and centrifugation. In a preferred embodiment, the precipitate is separated from the suspension using centrifugation.

At step 80, the method 70 includes calcining the precipitate at a temperature of 400-800° C., more preferably 550 to 650° C., and more preferably 600° C. for 1-24 hours, more preferably 1.5 to 5 hours, and more preferably 2 hours to form the catalyst. The calcination is carried out by heating it to a high temperature under a restricted supply of ambient oxygen. This is performed to remove impurities or volatile substances and to incur thermal decomposition. Typically, the calcination is carried out in a furnace, preferably equipped with a temperature control system, which may provide a heating rate of up to 50° C./min, preferably up to 40° C./min, preferably up to 30° C./min, preferably up to 20° C./min, preferably up to 10° C./min, preferably up to 5° C./min, to form the catalyst.

EXAMPLES

The following examples demonstrate a method of reducing carbon dioxide ($CO_2$) using $Fe_2TiO_5$ nanosheets. The examples are provided solely for illustration and are not to be construed as limitations of the present disclosure, as many variations thereof are possible without departing from the spirit and scope of the present disclosure.

Figure 2:
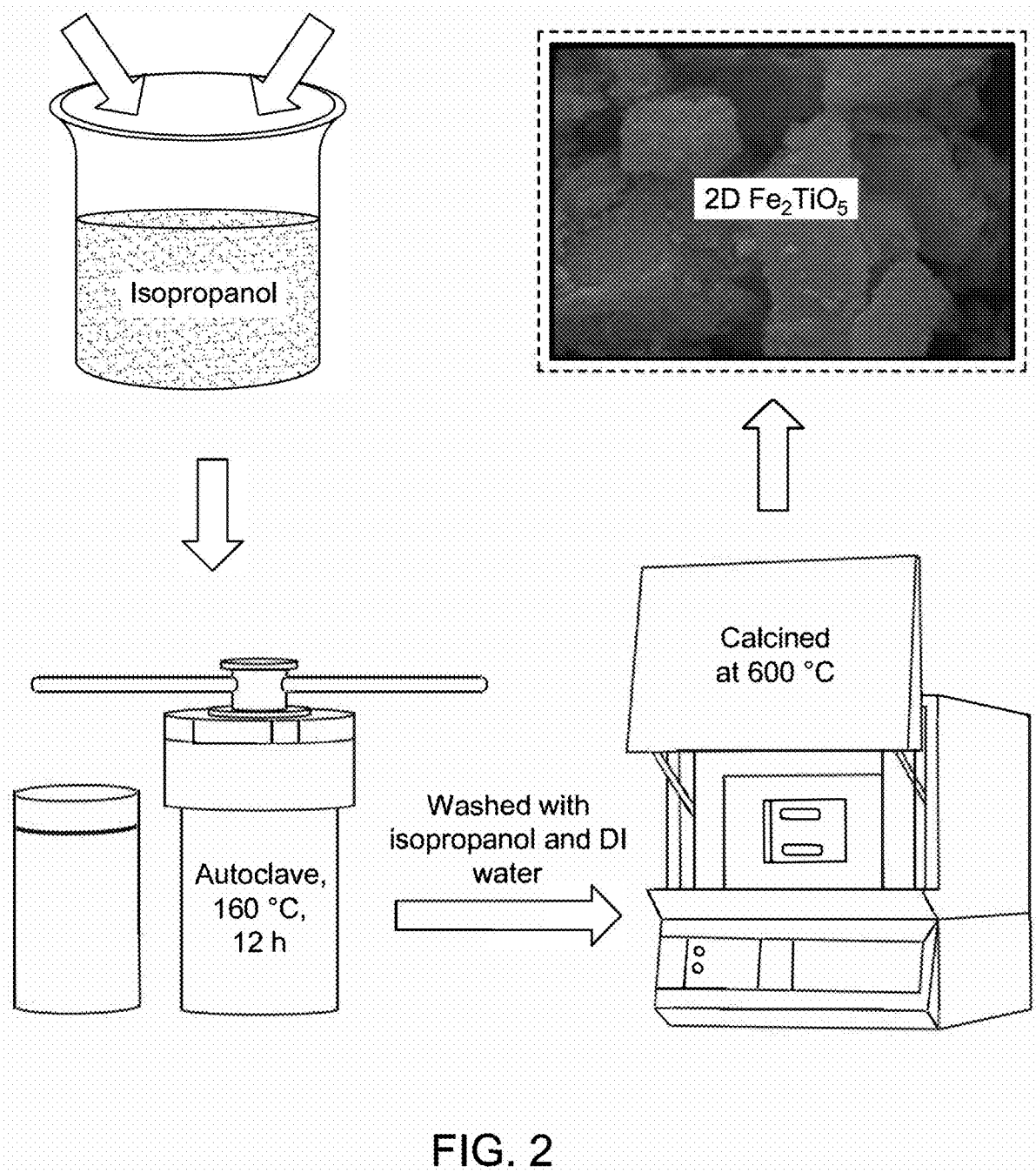
FIG. 2 is a schematic illustration depicting a formation process of $Fe_2TiO_5$ nanosheets, according to certain embodiments.

Example 1: Synthesis of $Fe_2TiO_5$ Nanosheets 5.02 millimoles (mmol) of $Fe(NO_3)_3 \cdot 9H_2O$ was dissolved in 50 milliliters (mL) of isopropanol with stirring. Following this, a pre-determined amount of titanium isopropoxide was introduced into the mixture under the same stirring conditions. The resultant solution underwent continuous stirring for 4 hours before being transferred to a Teflon-lined stainless-steel autoclave and subjected to heating at 160 degrees Celsius (° C.) for a duration of 12 hours. After cooling, the suspension underwent centrifugation, followed by washing with isopropanol and deionized water, and then drying in an oven at 80° C. for 12 hours. The resulting dried intermediate was subjected to calcination at 600° C. for 2 hours, yielding $Fe_2TiO_5$. The schematic illustration for fabricating the $Fe_2TiO_5$ nanosheets is depicted in FIG. 2.

Example 2: Photocatalytic Activity Test

Figure 3:
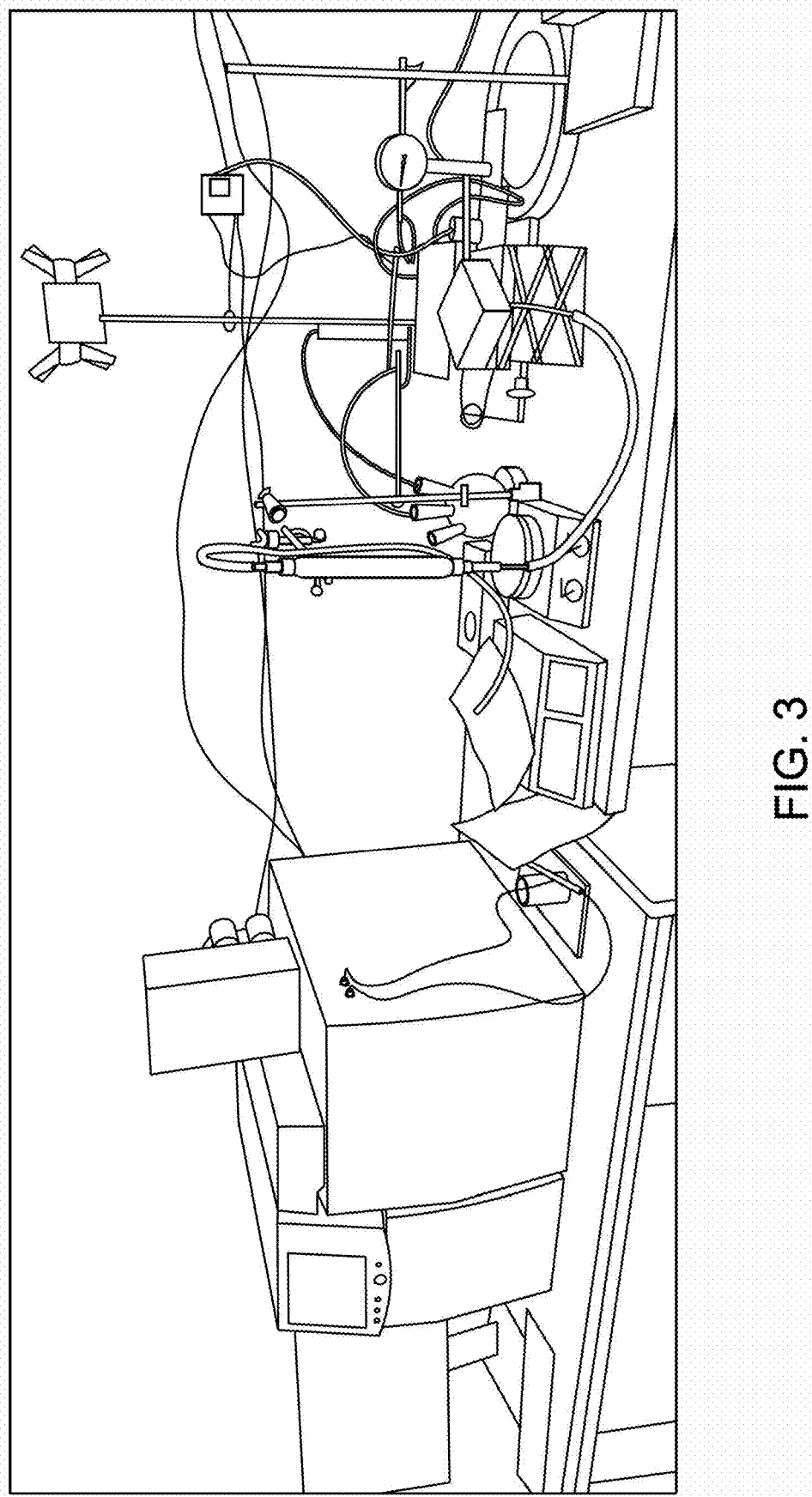
FIG. 3 depicts an experimental setup for photocatalytic carbon dioxide ($CO_2$) conversion with water ($H_2O$), according to certain embodiments.

The as-prepared photocatalysts were tested for photocatalytic conversion of $CO_2$ in a gaseous phase fixed-bed photoreactor, as shown in FIG. 3. A 50 watts (W) LED flood light, coupled with a concentrator, served as the illumination source to activate the photocatalytic reactions, facilitated by a quartz window to adjust light involvement. 150 milligrams (mg) of powder photocatalysts were dispersed at the bottom of the photoreactor to ensure proper distribution. Prior to introducing reactant gases, the reactor underwent nitrogen purging to eliminate other gases. High purity compressed $CO_2$, regulated by a mass flow controller, was passed through a water saturator for moisture carriage. For continuous $CO_2$ reduction, gas flowed through the reactor at a rate of 10 milliliters per minute (mL/min). Product analysis employed an online gas chromatograph (GC) with a flame ionization detector (FID) and a thermal conductivity detector (TCD) (GC/FID/TCD). In the absence of light irradiation or catalysts, carbon-containing products were not detected.

Example 3: Catalyst Characterization

Figure 4:
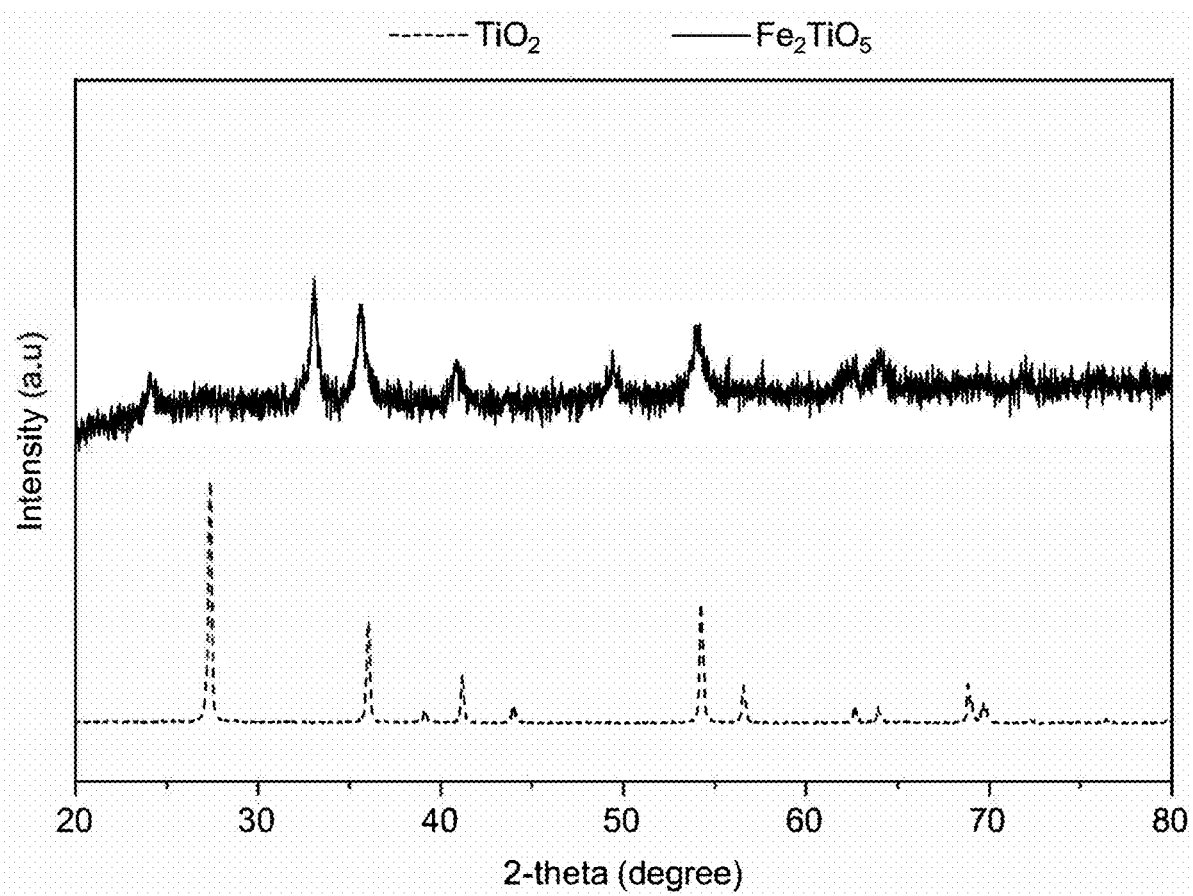
FIG. 4 shows X-ray diffraction (XRD) patterns of $TiO_2$ and $Fe_2TiO_5$, according to certain embodiments.

X-ray diffraction (XRD) analysis was employed to investigate the crystal phase and structure of photocatalysts, as shown in FIG. 4. $TiO_2$ displayed several diffraction peaks, which are characteristics of the $TiO_2$ photocatalyst. The pure $Fe_2TiO_5$ exhibited distinct peaks at 2θ values of 24.2°, 33.1°, 35.7°, 40.8°, 49.4°, 54.1°, and 62.5°, corresponding to the (101), (230), (301), (240), (430), (060), and (232) crystal planes of monoclinic $Fe_2TiO_5$ (JCPDS: 076-2372), respectively.

Figure 5A:
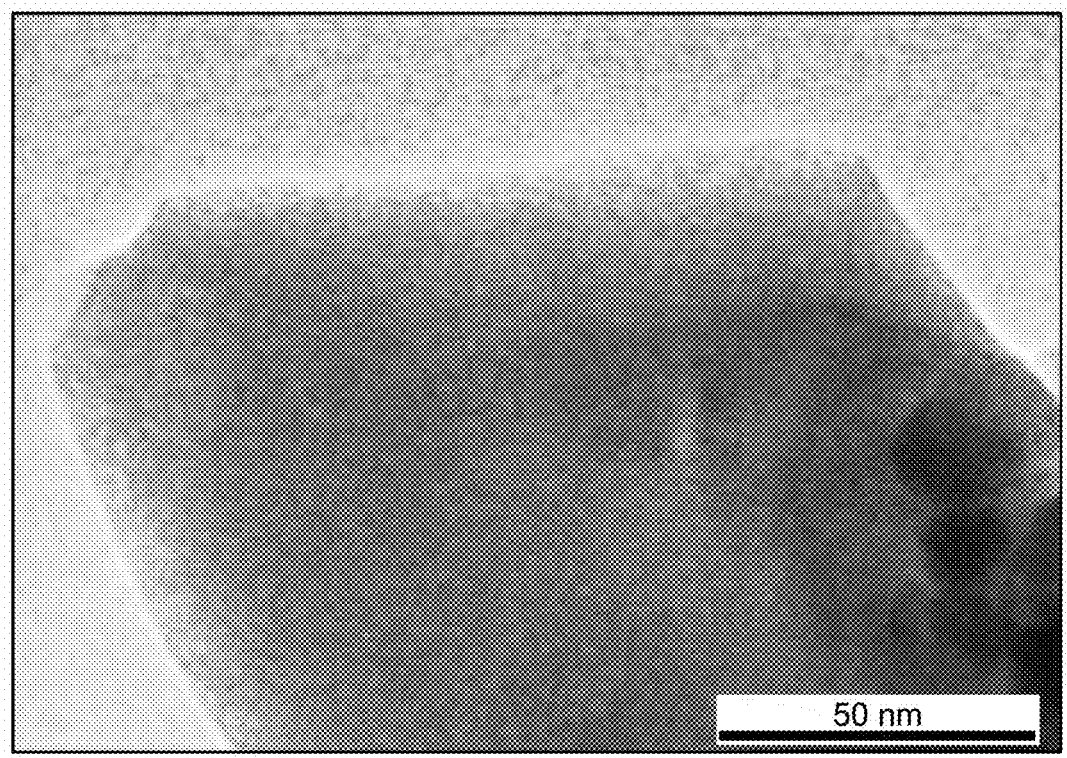
FIG. 5A is a transmission electron microscopy (TEM) image of $Fe_2TiO_5$ nanosheets, according to certain embodiments.
Figure 5B:
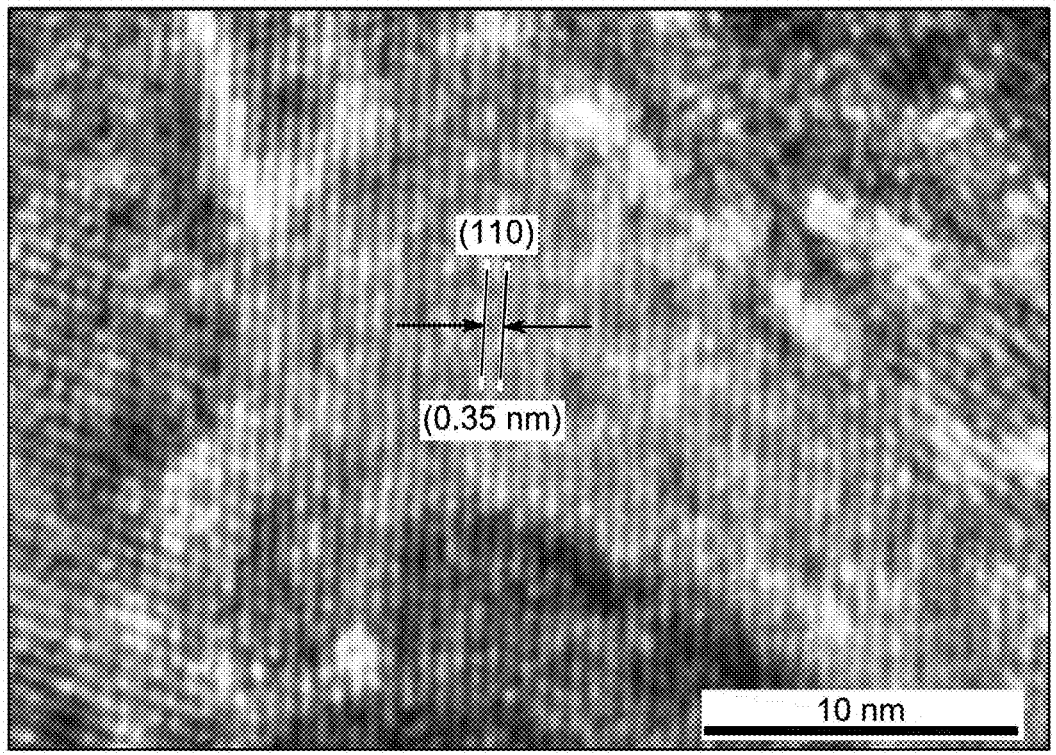
FIG. 5B is a high-resolution transmission electron microscopy (HRTEM) image depicting lattice fringes of $Fe_2TiO_5$ nanosheets, according to certain embodiments.
Figure 5C:
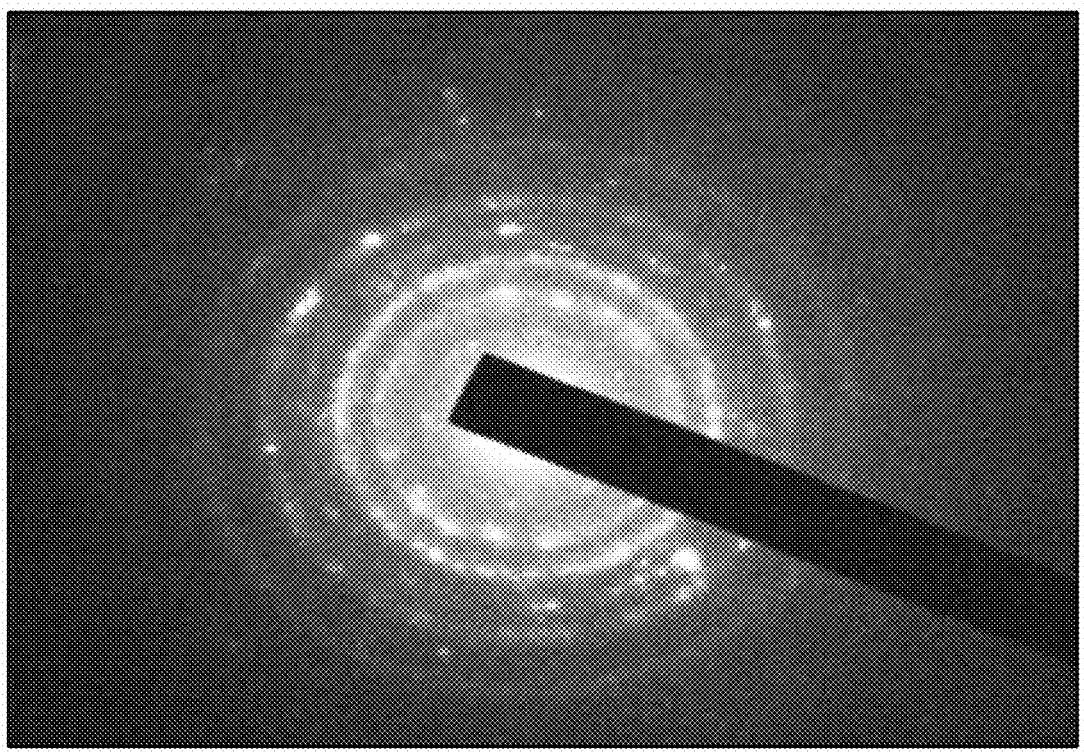
FIG. 5C is an optical image depicting selected area electron diffraction (SAED) pattern of $Fe_2TiO_5$ nanosheets, according to certain embodiments.
Figure 5D:
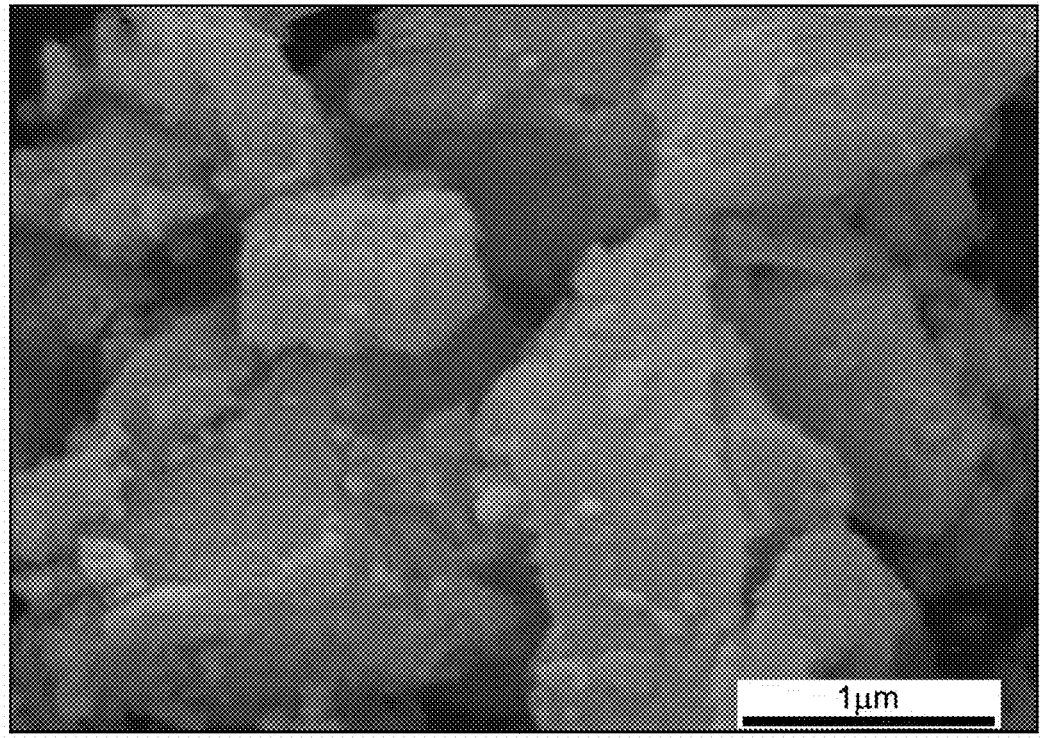
FIG. 5D is a scanning electron microscopy (SEM) image of $Fe_2TiO_5$ nanosheets, according to certain embodiments.
Figure 5E:
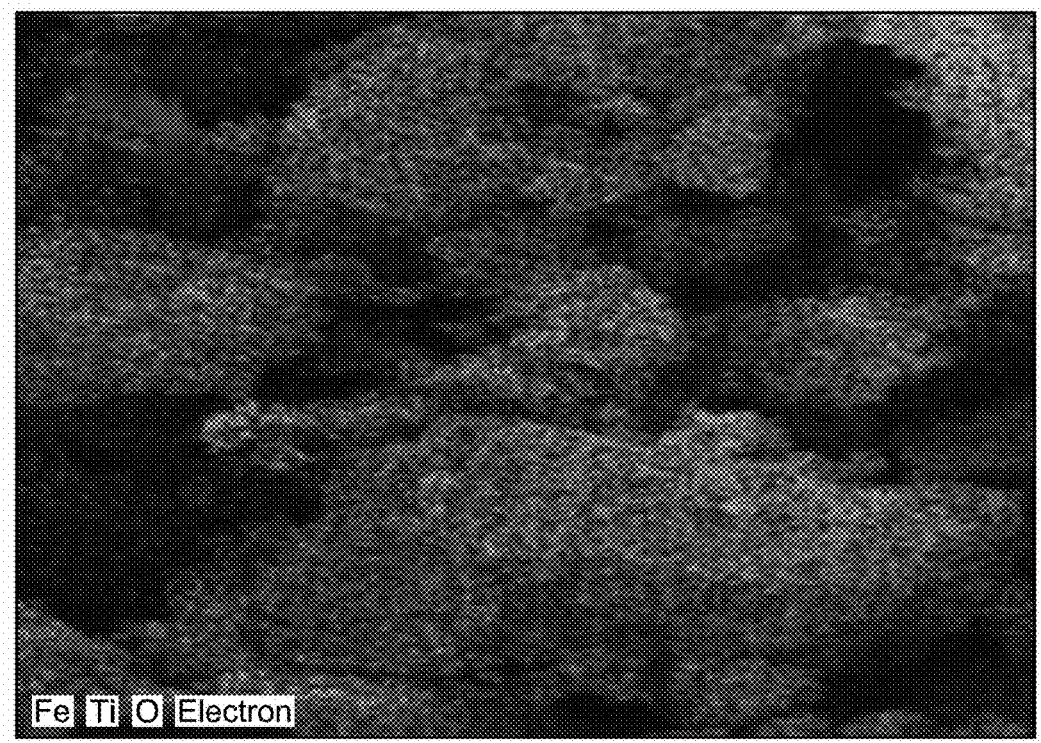
FIG. 5E is a field emission scanning electron microscopy (FESEM) image of $Fe_2TiO_5$ nanosheets, according to certain embodiments.
Figure 5F:
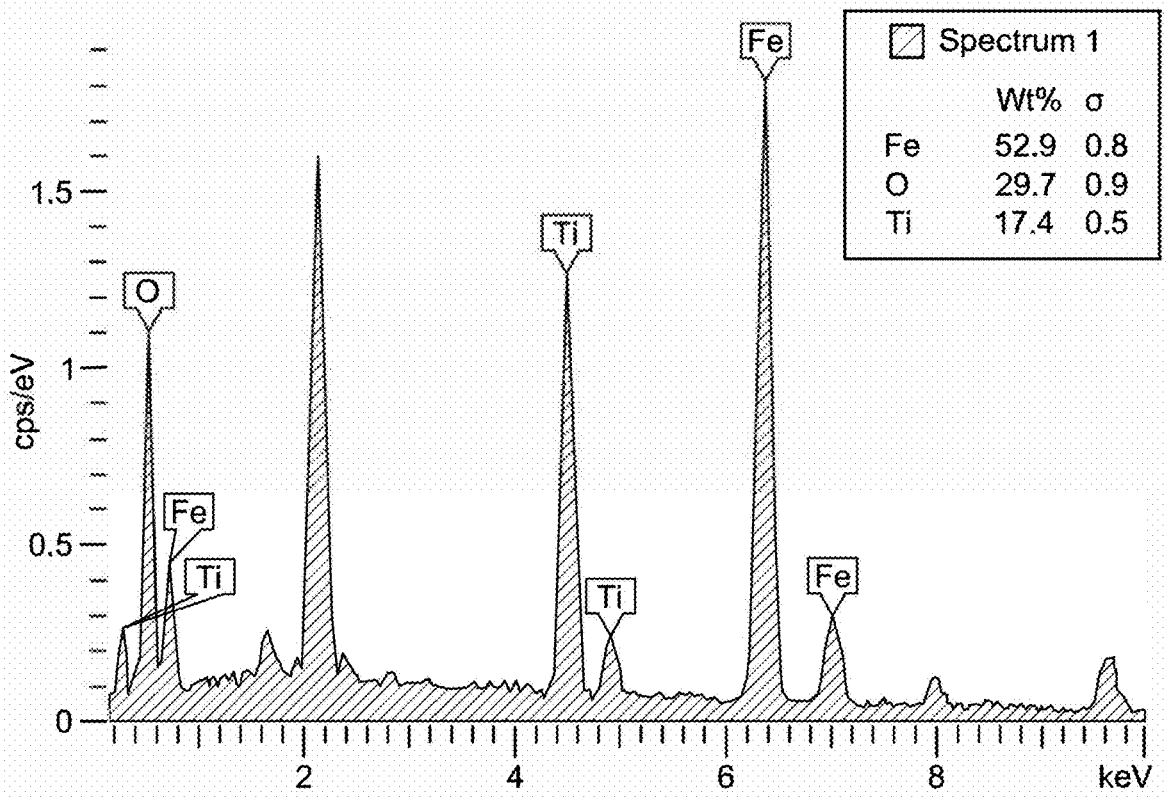
FIG. 5F depicts an energy-dispersive X-ray (EDX) spectrum of $Fe_2TiO_5$ nanosheets according to certain embodiments.
Figure 5G:
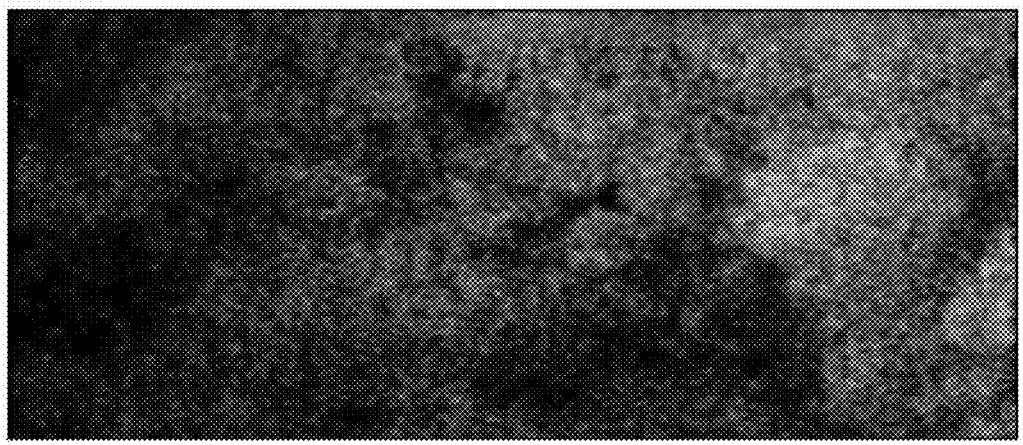
FIG. 5G is an SEM image of $Fe_2TiO_5$ nanosheets depicting the presence of iron, according to certain embodiments.
Figure 5H:
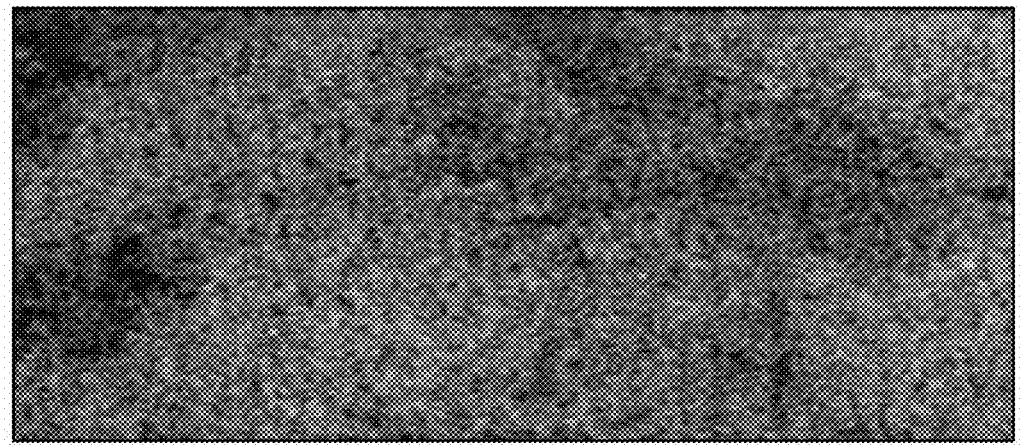
FIG. 5H is an SEM image of $Fe_2TiO_5$ nanosheets depicting the presence of oxygen, according to certain embodiments.
Figure 5I:
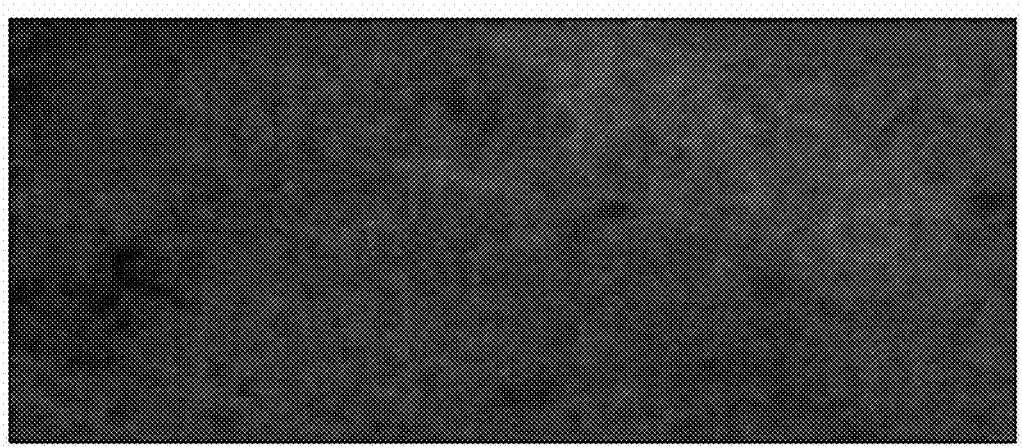
FIG. 5I is an SEM image of $Fe_2TiO_5$ nanosheets depicting the presence of titanium, according to certain embodiments.

The investigation of $Fe_2TiO_5$ nanosheets involved the examination of morphology and microstructural features using field emission scanning electron microscopy (FE-SEM) and high-resolution transmission electron microscopy (HRTEM), as depicted in FIGS. 5A-5I. The transmission electron microscopy (TEM) images of the pure $Fe_2TiO_5$ photocatalyst, are illustrated in FIGS. 5A-5C. Further, FIG. 5A displays the microstructure of $Fe_2TiO_5$, composed of numerous compact nanosheets. The interplanar distance was measured at 0.35 nm, corresponding to the (110) plane of $Fe_2TiO_5$, as illustrated in FIG. 5B. The selected area electron diffraction (SAED) pattern in FIG. 5C exhibits a clear polycrystalline ring, indicating the good crystallization of $Fe_2TiO_5$ nanosheets. The SEM image of $Fe_2TiO_5$ nanosheets is depicted in FIG. 5D, and it can be observed that $Fe_2TiO_5$ has a significant number of nanosheets. The FESEM (FIG. 5E) and energy dispersive X-ray (EDX) analysis of $Fe_2TiO_5$ photocatalyst is shown in FIG. 5F. The EDX plot of the elements of $Fe_2TiO_5$ nanosheets is depicted in FIG. 5G-FIG. 5I. FIG. 5G and FIG. 5I verifies the existence of iron, oxygen, and titanium, respectively, in the $Fe_2TiO_5$ photocatalyst. These results indicate the effective development of $Fe_2TiO_5$ nanosheets, potentially resulting in heightened photocatalytic performance.

Figure 6A:
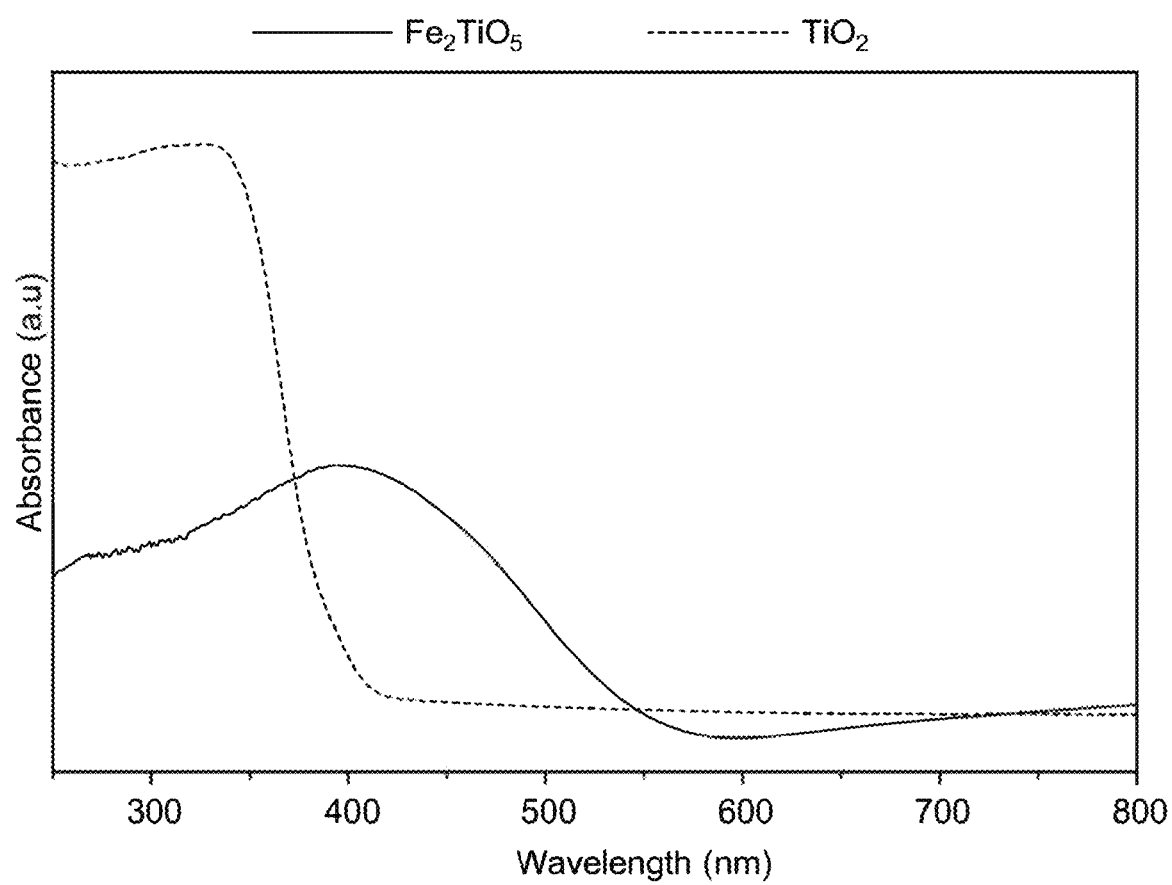
FIG. 6A shows diffuse reflectance (DR) ultra-violet (UV) visible spectra of $TiO_2$ and $Fe_2TO_5$ nanosheets, according to certain embodiments.

FIG. 6A illustrates the UV-visible diffuse reflectance absorbance spectra for the $Fe_2TiO_5$ sample. As can be seen from FIG. 6A, the $Fe_2TiO_5$ nanosheets exhibit strong absorption intensities within the visible light range, especially when compared to $TiO_2$. The energy band gap ($E_{bg}$) of the $Fe_2TiO_5$ sample was determined using the Tauc equation, as depicted in equation (1).

$$E_g(eV) = \frac{1240}{\lambda} \quad (1)$$

The $Fe_2TiO_5$ sample displays a wavelength of 587 nm, corresponding to a calculated $E_g$ value of 2.1 eV. The conduction band position ($E_{CB}$) of the $Fe_2TiO_5$ semiconductor was determined using equation (2).

$$E_{VB} = E_{CB} + E_{bg} \quad (2)$$

Figure 6B:
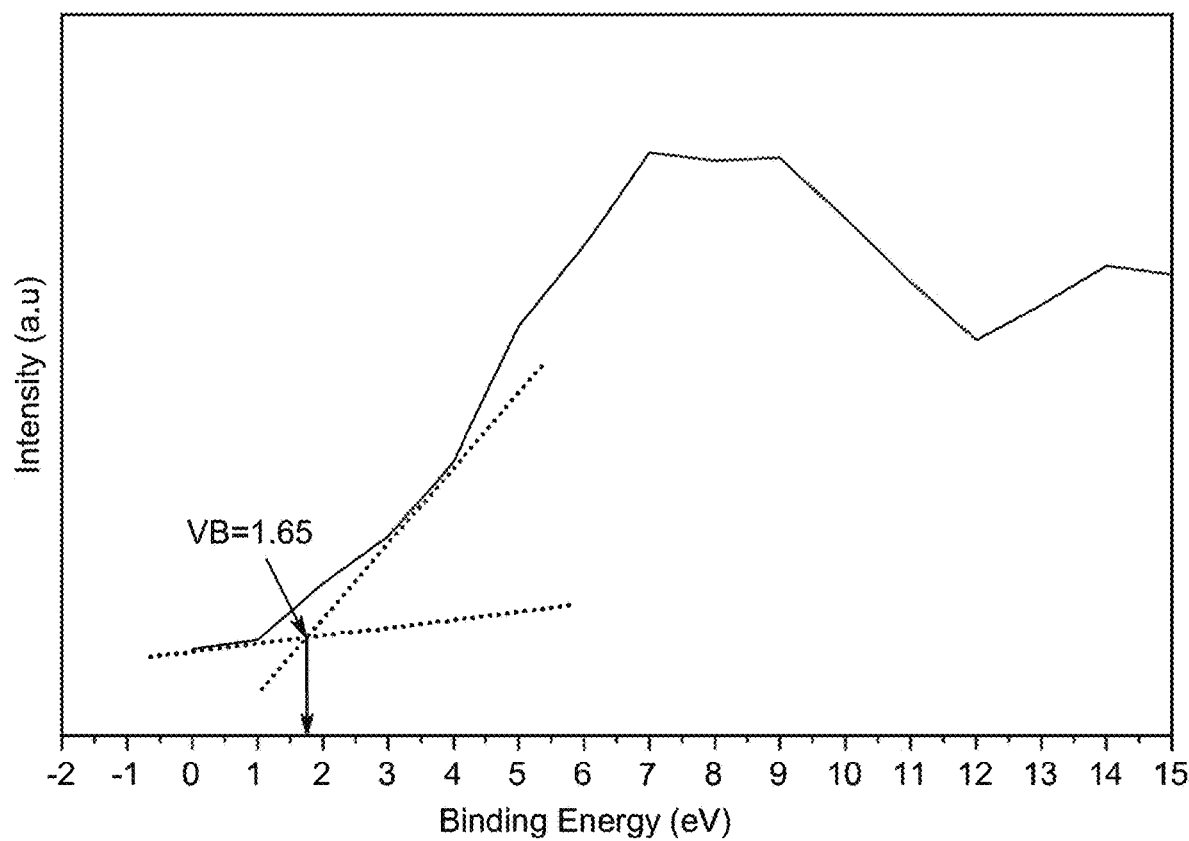
FIG. 6B is a graph depicting band gap energy calculations from absorption spectra of $Fe_2TO_5$ nanosheets, according to certain embodiments.

Valence band X-ray photoelectron spectroscopy (VB-XPS) was utilized to examine the valence band of the $Fe_2TiO_5$ sample. As illustrated in FIG. 6B, the valence band edges of $Fe_2TiO_5$ were observed to be situated around 1.65 eV. The energy band gap ($E_{bg}$) for $Fe_2TiO_5$ was determined to be 2.1 eV. Therefore, the conduction band of the $Fe_2TiO_5$ sample was calculated to be at −0.45 eV.

Example 4: Photocatalytic Activity and Stability

The experiments examining the conversion of $CO_2$ with $H_2O$ were conducted in the presence of visible light. During these tests, it was observed that when the lamp was turned off, no carbon-containing compounds were present in the reaction system. Conversely, under light exposure, a consistent generation of CH$_3$OH and dimethyl ether (DME) was identified. This observation indicates that both the samples and the photoreactors were effectively cleaned, and any carbon-containing compounds were exclusively formed through the reduction of CO$_2$.

Figure 7:
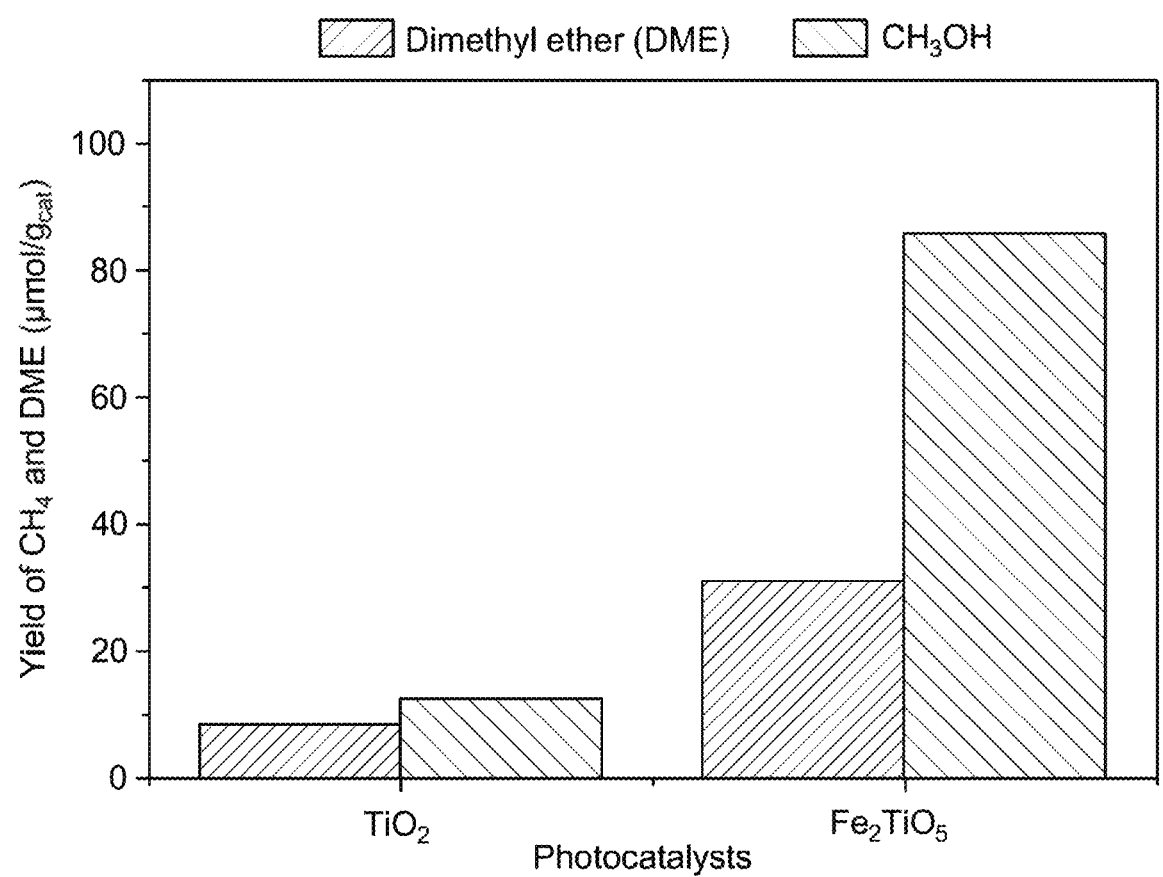
FIG. 7 shows the yield of $CH_3OH$ and dimethyl ether (DME) over $TiO_2$ and $Fe_2TO_5$ photocatalysts at an irradiation time of 1 hour, room temperature, and atmospheric pressure, according to certain embodiments.

The effect of varying TiO$_2$ and Fe$_2$TiO$_5$ samples on the photoactivity of photocatalytic CO$_2$ conversion under visible light is demonstrated in FIG. 7. The assessment of the photocatalysts focused on the yield of CH$_3$OH and DME, the two resulting products. The pure TiO$_2$ photocatalyst demonstrated minimal CO$_2$ reduction and exhibited poor efficiency in generating CH$_3$OH and DME. However, the utilization of the Fe$_2$TiO$_5$ nanosheets significantly increased the production of CH$_3$OH and DME. This improvement is ascribed to the effective absorption of visible light by the nanosheets, proficient charge transfer characteristics, and heightened electron mobility achieved through the coupling of iron with titanium using the single-step hydrothermal process.

Figure 8:
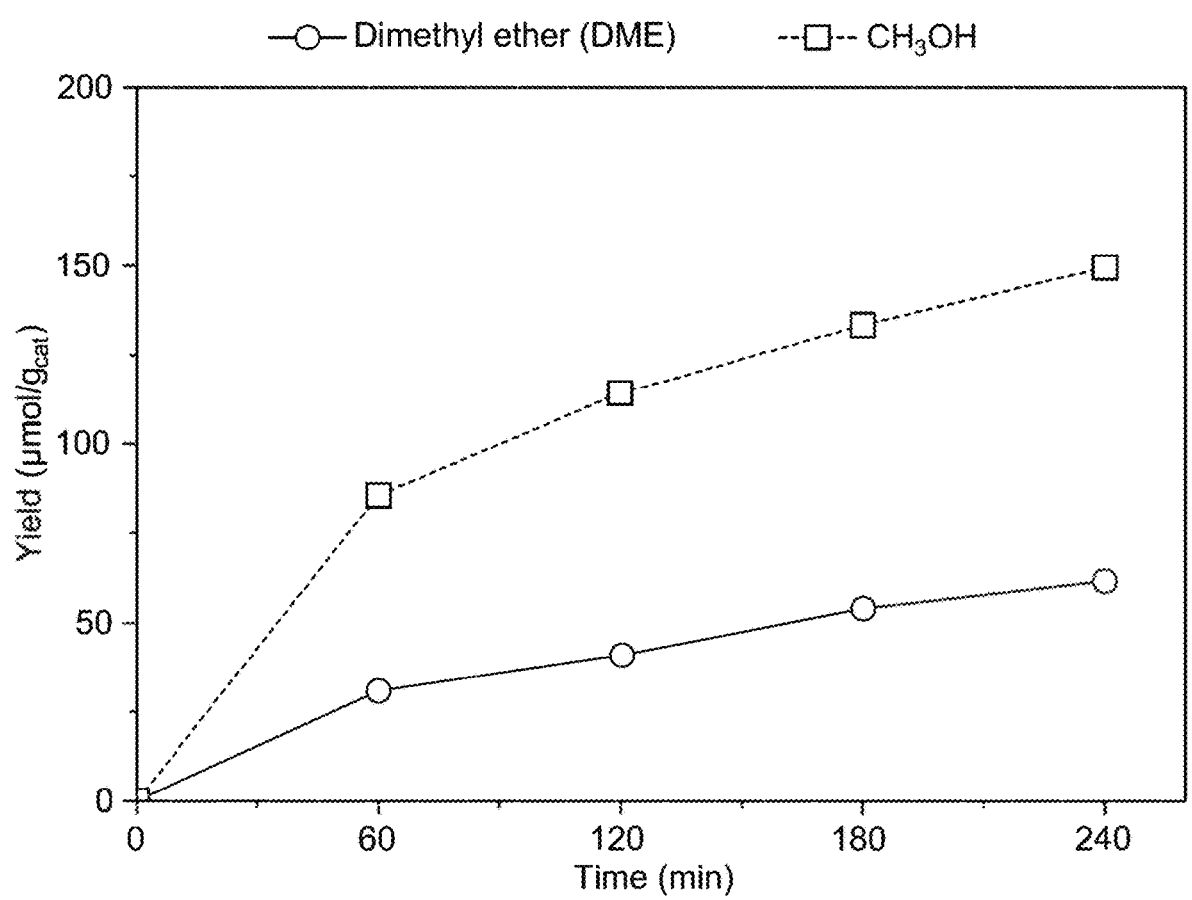
FIG. 8 shows the yield of $CH_3OH$ and dimethyl ether (DME) with $TiO_2$ and $Fe_2TO_5$ photocatalysts over time, according to certain embodiments.

The influence of irradiation times on the visible-light-driven photocatalytic CO$_2$ conversion with H$_2$O to CH$_3$OH and DME over Fe$_2$TiO$_5$ nanosheets are illustrated in FIG. 8. The gradual increase in CH$_3$OH and DME generation becomes evident as the irradiation time extends. When employing Fe$_2$TiO$_5$ nanosheets, CH$_3$OH emerges as the main product in the process of CO$_2$ photoreduction. The catalyst exhibits sustained activity even after 4 hours of continuous irradiation, ensuring ongoing production of CH$_3$OH and DME. Consequently, these innovative Fe$_2$TiO$_5$ nanosheets offer heightened photoactivity and stability, thereby enhancing the conversion of CO$_2$ into solar fuels.

Example 5: Reaction Mechanism

Fe$_2$TiO$_5$ nanosheets were used as photocatalysts to assess the photocatalytic activity of CO$_2$ reduction to CH$_3$OH and DME. Key reaction steps are succinctly outlined in equations 3 to 7 during the reduction process.

$$Fe_2TiO_5 + h\nu \rightarrow h^+ + e^- \quad (3)$$

$$H_2O + h^+ \rightarrow OH^- + H^+ \quad (4)$$

$$CO_2 + e^- \rightarrow CO_2^- \quad (5)$$

$$CO_2 + 6H^+ + 6e^- \rightarrow CH_3OH + H_2O \quad (6)$$

$$CO_2 + 12H^+ + 12e^- \rightarrow C_2H_6O + H_2O \quad (7)$$

Equation 3 illustrates the generation of electron-hole pairs upon photoexcitation. The conversion of CO$_2$ takes place in the conduction band through electron participation, whereas holes in the valence band facilitate the oxidation of H$_2$O, as elucidated in equations 4 and 5. The mechanisms for producing CH$_3$OH and DME via the reduction of CO$_2$ involving 6 and 12 electrons are detailed in equations 6 to 7. The investigation of photoactivity and reaction pathways provides valuable insights into the reaction mechanism.

Figure 9:
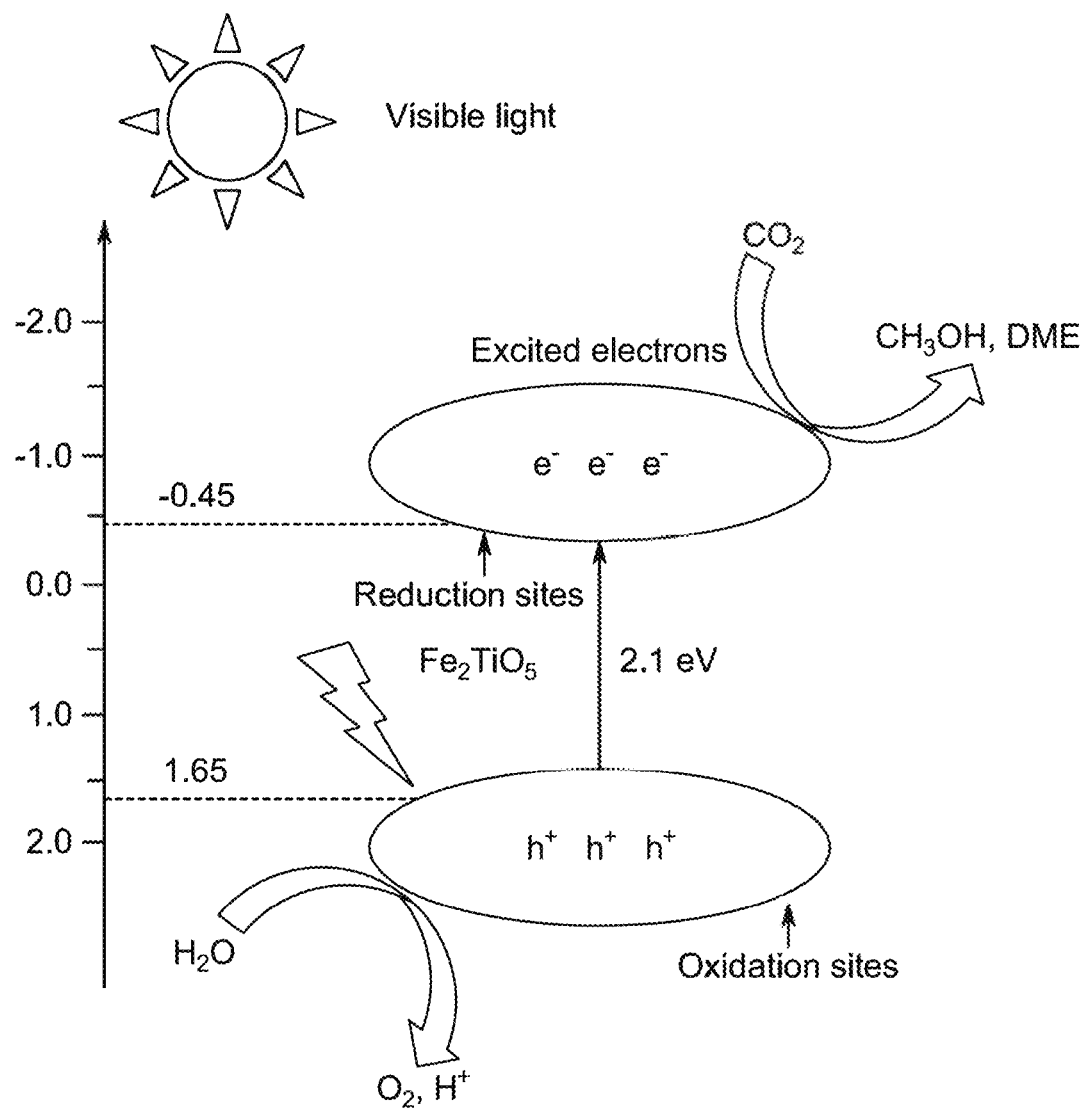
FIG. 9 is a schematic illustration depicting a reaction mechanism proposed for the photoreduction of $CO_2$ to $CH_3OH$ and DME over $Fe_2TO_5$ nanosheets under visible light, according to certain embodiments.

The reaction mechanism for the production of CH$_3$OH and DME using Fe$_2$TiO$_5$ nanosheets is illustrated in FIG. 9. When exposed to visible light, electrons excited from the valence band (VB) of Fe$_2$TiO$_5$ nanosheets migrate to the conduction band (CB). Holes in the VB of Fe$_2$TiO$_5$ nanosheets interact with H$_2$O, leading to the generation of O$_2$ and H$^+$. Concurrently, absorbed CO$_2$ molecules undergo reduction to form CH$_3$OH and DME, facilitated by the enriched electrons on the surface of Fe$_2$TiO$_5$ nanosheets. In the context of CO$_2$ reduction with H$_2$O, Fe$_2$TiO$_5$ nanosheets predominantly yield CH$_3$OH as the main product, due to the suitable reduction potential of CO$_2$/CH$_3$OH (−0.38 V). The reaction is more favorable for CH$_3$OH production as the reduction potential of CO$_2$/CH$_3$OH (−0.38 V) is lower than the conduction band of Fe$_2$TiO$_5$ nanosheets. While C$_2$H$_6$O (CME) requires more electrons and has a conduction band far to that of CH$_3$OH compared to Fe$_2$TiO$_5$ nanosheets, the proper band alignment of Fe$_2$TiO$_5$ contributes to the selective production of CH$_3$OH during CO$_2$ conversion under visible light. Consequently, the Fe$_2$TiO$_5$ nanosheets exhibit significantly enhanced CH$_3$OH production due to effective visible light absorption, a suitable band structure, and higher electron mobility with inhibited recombination.

To summarize, the Fe$_2$TiO$_5$ nanosheets of the present disclosure demonstrate significant performance, yielding 149.5 μmol per gram of the catalyst (μmole/g-cat) of CH$_3$OH and 61.6 μmole/g-cat of dimethyl ether (DME), respectively. Compared to TiO$_2$ samples, the desired hierarchical nanosheets of Fe$_2$TiO$_5$ exhibit 3.8-fold and 4.1-fold higher efficiency in CH$_3$OH and DME production, highlighting the advantages of their structure. The hierarchical nanosheets of Fe$_2$TiO$_5$ facilitate electron transfer to CO$_2$ due to their unique structure, providing efficient electron pathways and electron storage sites within the nanosheets, thereby enhancing photoactivity. Moreover, the extended stability of Fe$_2$TiO$_5$ in CO$_2$ conversion further confirms the controllable selectivity and stability offered by the hierarchical nanosheets structure. The fabrication of hierarchical structures holds promise for advancing high-performance photocatalysts for solar fuel production through CO$_2$ conversion.

Numerous modifications and variations of the present disclosure are possible in light of the above teachings. It is therefore to be understood that within the scope of the appended claims, the invention may be practiced otherwise than as specifically described herein.

The invention claimed is:
1. A method of reducing carbon dioxide, comprising:
    contacting a catalyst and the carbon dioxide; and
    irradiating the catalyst and the carbon dioxide with visible light,
    wherein on the irradiating the carbon dioxide is reduced to a conversion product,
    wherein the catalyst comprises Fe$_2$TiO$_5$,
    wherein particles of the Fe$_2$TiO$_5$ are in a form of nanosheets,
    wherein the nanosheets have an average width of 200-800 nm, and
    wherein the nanosheets form a hierarchical structure of two or more of the nanosheets stacked on top of one another.
2. The method of claim 1, wherein the nanosheets are crystalline.
3. The method of claim 1, wherein the nanosheets have an interplanar distance of 0.3-0.4 nanometers (nm).
4. The method of claim 1, wherein the nanosheets have an average length of 1-3 micrometers (μm).
5. The method of claim 1, wherein the catalyst comprises 45-55 wt. % Fe, 25-35 wt. % O, and 15-25 wt. % Ti, based on a total weight of the catalyst.
6. The method of claim 1, wherein the catalyst absorbs light from 200-550 nm.
7. The method of claim 1, wherein the catalyst has a peak light absorbance from 375-425 nm.

8. The method of claim 1, wherein the catalyst has a band gap of 1.9-2.2 electron volts (eV).

9. The method of claim 1, wherein the catalyst does not comprise $Fe_2O_3$ or $TiO_2$.

10. The method of claim 1, wherein the carbon dioxide is in a gaseous state.

11. The method of claim 1, wherein the carbon dioxide is in an aqueous solution.

12. The method of claim 1, wherein the conversion product is at least one selected from the group consisting of methanol and dimethyl ether.

13. The method of claim 1, wherein the irradiating is for 1 min to 10 hours.

14. The method of claim 1, wherein the visible light has a wavelength of 400-700 nm, and a power of 10-100 watts (W).

15. The method of claim 1, wherein the conversion product is methanol, and a yield of the methanol is 120-160 µmol per gram of the catalyst after irradiating for 4 hours.

16. The method of claim 1, wherein the conversion product is dimethyl ether, and a yield of the dimethyl ether of 40-60 micromoles per gram (µmol) of the catalyst after irradiating for 4 hours.

17. The method of claim 1, wherein the catalyst has a higher conversion to the conversion product than $TiO_2$ under the same conditions.

18. The method of claim 1, wherein the $Fe_2TiO_5$ is made by a method comprising:
   mixing an iron salt in a solvent to form a first mixture;
   adding titanium isopropoxide to the first mixture to form a second mixture;
   heating the second mixture in an autoclave at a temperature of 150-200° C. for 1-24 hours to form a suspension;
   separating a precipitate from the suspension; and
   calcining the precipitate at a temperature of 400-800° C. for 1-24 hours to form the catalyst.

* * * * *